(12) United States Patent
Vidgen (10) Patent No.: US 7,090,638 B2
(45) Date of Patent: Aug. 15, 2006

(54) SYSTEM AND METHOD FOR OPTIMIZED DIETARY MENU PLANNING

(76) Inventor: Edward Vidgen, 32 Ridley Gardens, Toronto (CA) M6R 2TB ( * ) Notice: Subject to any disclaimer, the term of this patent is extended or adjusted under 35 U.S.C. 154(b) by 559 days.

(21) Appl. No.: 10/162,283

(22) Filed: Jun. 3, 2002

(65) Prior Publication Data

US 2003/0225731 A1  Dec. 4, 2003

(51) Int. Cl.
*A61B 5/00* (2006.01)
(52) U.S. Cl. ...................... 600/300; 128/921
(58) Field of Classification Search ........ 600/300–301; 128/921; 434/127; 235/375; 705/26–27, 705/10, 15
See application file for complete search history.

(56) References Cited

U.S. PATENT DOCUMENTS

| | | | |
|---|---|---|---|
| 4,951,197 A | 8/1990 | Mellinger | |
| 4,954,954 A | 9/1990 | Madsen et al. | |
| 5,233,520 A | 8/1993 | Kretsch et al. | |
| 5,412,560 A | 5/1995 | Dennision | |
| 5,412,564 A | 5/1995 | Ecer | |
| 5,673,691 A * | 10/1997 | Abrams et al. | 600/300 |
| 5,836,312 A | 11/1998 | Moore | |
| 5,839,901 A | 11/1998 | Karkanen | |
| 5,954,640 A | 9/1999 | Szabo | 705/10 |
| 6,370,513 B1 * | 4/2002 | Kolawa et al. | 705/10 |

FOREIGN PATENT DOCUMENTS

| | | |
|---|---|---|
| WO | WO 00/28460 | 5/2000 |
| WO | W0 01/65460 | 9/2001 |
| WO | WO 01/97154 | 12/2001 |

\* cited by examiner

*Primary Examiner*—Max F. Hindenburg
*Assistant Examiner*—Michael Astorino
(74) *Attorney, Agent, or Firm*—Townsend and Townsend and Crew LLP (57) ABSTRACT

A dietary menu planning system. The dietary menu planning system receives personal characteristics and food preferences for an individual. The personal characteristics includes a desired physiological rate of change for the individual. Based on the physiological rate of change and other personal characteristics, a set of dietary constraints is developed for the individual. A dietary menu plan is created for the individual including food items selected by the individual and with quantities determined to maximize the food preferences of the individual while satisfying the dietary constraints. The creation of the dietary menu plan includes applying an optimization function to maximize the food preferences. The dietary menu planning system is implemented as a stand-alone application for a computer or as a networked-system, for example, as a fee-for-service basis through the Internet.

20 Claims, 6 Drawing Sheets

| FOOD ←—310 | MFG ←—320 | RATING ←—330 |
|---|---|---|
| ORANGE JUICE, RAW | | 66 |
| ORANGE JCE, FRZ, CONC | | |
| CHOC. ENRICHED RICE BEVERAGE (RICE DREAM) | IMAGINE FOODS | 50 |
| LIFEWAY KEFIR | LIFEWAY | 24 |
| BETA BLAST BETA CAROTENE COCKTAIL | LOBLAWS | |
| LITE EGG NOG | LOBLAWS | |
| LITE NON – DAIRY SOY BEVERAGE | LOBLAWS | |
| FAT FREE MILK BEVERAGE | LOBLAWS | |
| FAT FREE ICED CAFÉ AU LAIT MILK BEVERAGE | LOBLAWS | 20 |
| FAT FREE CHOCOLATE MILK BEVERAGE | LOBLAWS | |
| FAT FREE EGG NOG | LOBLAWS | |
| VITA SOY COCOA | VITASOY | |
| GREEN TEA CHAI SOY DRINK | VITASOY | 12 |
| BREAD, ITALIAN | | 11 |
| WHEAT 'N ONION CRACKERS | LOBLAWS | |
| WHEAT BRAN 'N RYE CRACKERS | LOBLAWS | 22 |
| SESAME 'N WHEAT CRACKERS | LOBLAWS | |
| ORGANIC RICE CAKES | LOBLAWS | 3 |
| BRAN LOAF | LOBLAWS | 36 |
| MULTIGRAIN LOAF | LOBLAWS | 29 |
| 60% WHOLE WHEAT CRACKERS | LOBLAWS | |
| LOW FAT MUESLI MUFFINS | LOBLAWS | 0 |
| 11 REASONS WHITE LOAF | LOBLAWS | |
| SIERRA TRAIL FRUIT AND NUT BAR | LOBLAWS | -30 |
| MULTIGRAIN PRETZELS | LOBLAWS | |
| BLACKBEAN BAKED POTATO CHIPS | LOBLAWS | 48 |
| SOUR CREAM & ONION BAKED POT CHIPS | LOBLAWS | |
| BARBECUE BAKED POTATO CHIPS | LOBLAWS | -55 |
| BAKED NOT FRIED POTATO CHIPS | LOBLAWS | |
| SALT & VINEGAR BAKED CHIPS | LOBLAWS | |
| FIG BARS | | 33 |
| COOKIES, OATMEAL / RAISIN | | 8 |
| CANDIES, MILKCHOC / PLAIN | | |
| APPLE PIE | AMYS KITCHEN | 53 |
| SOYA DESSERT COCOA FLAVOR | PROVAMEL | 80 |
| SOYA DESSERT HAZELNUT FLAVOR | PROVAMEL | |
| SOYA DESSERT VANILLA FLAVOR | PROVAMEL | |
| COOKIES, CHOC CHIP | | |
| NATURE VALLEY GRANOLA | | 0.5 |
| OATS, ROLLED | | 14 |
| MUSHROOM CHEESE ROUNDS | LOBLAWS | |
| YOGURT, SKIM | | |
| FAT- FREE (0.1% M.F.) PLAIN YOGURT | LOBLAWS | 27 |
| ALL – NATURAL LIGHT (1% M.F.) PLAIN YOGURT | LOBLAWS | 15 |
| LEMON LOW FAT YOGURT W / 7 GRAINS | LOBLAWS | |
| PASSION FT. LOW FAT YOGURT W / 7 GRAINS | LOBLAWS | |
| PEACH LOW FAT YOGURT W / 7 GRAINS | LOBLAWS | |
| RASP. LOW FAT YOGURT W / 7 GRAINS | LOBLAWS | |
| STRW. LOW FAT YOGURT W/ 7 GRAINS | LOBLAWS | |
| RED WINE | | 180 |
| APPLES | | |
| APRICOTS | | -19 |
| APRICOT DRIED | | |
| BANANAS | | -92 |
| DATES, DRY | | |
| GRAPES | | 23 |
| KIWI FRUIT | | 21 |
| MELON, CANTALOUPE | | |
| ORANGES | | 10 |
| PEACHES | | 16 |
| PEACH, DRIED | | |
| PEARS | | 22 |
| PRUNES, DRIED | | |
| TOMATOES | | |
| GREEK SALAD | | |
| DATE SQUARE | | |

| FOOD | CODE | WEIGHT | KCAL | PROTEIN | CARB | FAT | MUFA | PUFA | SFA | FIBRE | CHOL |
|---|---|---|---|---|---|---|---|---|---|---|---|
| RASPBERRIES, RAW | 9302 | 900 | 234 | 8 | 50 | 0 | 0 | 0 | 0 | 67 | 0 |
| TABOULE SALAD | 137199 | 199 | 228 | 6 | 16 | 14 | 8 | 4 | 1 | 7 | 0 |
| ROASTED VEGETABLES IN A POCKET SANDWICH | 137216 | 887 | 1525 | 42 | 215 | 56 | 30 | 15 | 11 | 27 | 0 |
| CHOC. ENRICHED RICE BEVERAGE (RICE DREAM) | 137223 | 250 | 170 | 1 | 31 | 3 | 2 | 1 | 1 | 0 | 0 |
| BLACK BEAN VEGETABLE SOUP | 137230 | 250 | 121 | 7 | 19 | 1 | 1 | 0 | 0 | 6 | 0 |
| PLAN 1 | | 2486 | 2278 | 64 | 331 | 74 | 41 | 20 | 13 | 107 | 0 |
| AVOCADO, RAW, ALL VAR | 9037 | 47 | 71 | 1 | 4 | 7 | 5 | 1 | 1 | 3 | 0 |
| PRUNES, DRIED | 9291 | 222 | 527 | 6 | 123 | 1 | 1 | 0 | 0 | 16 | 0 |
| EXTRA FIRM TOFU | 109695 | 156 | 228 | 27 | 3 | 12 | 7 | 3 | 2 | 0 | 0 |
| RICE DREAM | 137193 | 250 | 127 | 1 | 26 | 2 | 2 | 0 | 0 | 0 | 0 |
| BLACK BEAN VEGETABLE ENCHILADA | 137229 | 237 | 228 | 7 | 32 | 7 | 5 | 2 | 1 | 4 | 0 |
| BUTTERNUT SOUP | 137276 | 190 | 228 | 4 | 40 | 4 | 3 | 0 | 1 | 4 | 0 |
| SOYA DESSERT COCOA FLAVOR | 137284 | 828 | 869 | 25 | 147 | 14 | 3 | 7 | 4 | 14 | 0 |
| PLAN 2 | | 1930 | 2278 | 71 | 372 | 67 | 26 | 13 | 8 | 41 | 0 |
| APRICOTS, RAW | 9021 | 62 | 18 | 0 | 4 | 0 | 0 | 0 | 0 | 1 | 0 |
| CURRANTS, ZANTE, DRIED | 9085 | 282 | 889 | 12 | 209 | 1 | 0 | 1 | 0 | 0 | 0 |
| SIMULATED FRANKFURTERS | 110342 | 100 | 228 | 24 | 9 | 11 | 2 | 7 | 2 | 0 | 0 |
| GREEN TEA CHAI SOY DRINK | 137224 | 250 | 125 | 7 | 15 | 4 | 1 | 3 | 1 | 2 | 0 |
| FAMILY SIZED BLACK BEAN VEG ENCHILADA | 137244 | 900 | 871 | 22 | 102 | 29 | 20 | 9 | 0 | 22 | 0 |
| POTATO: LEEK SOUP | 137280 | 250 | 138 | 8 | 30 | 6 | 4 | 3 | 0 | 5 | 0 |
| SOYA DESSERT HAZELNUT FLAVOR | 137285 | 9 | 11 | 0 | 2 | 0 | 0 | 0 | 0 | 0 | 0 |
| PLAN 3 | | 1853 | 2280 | 73 | 371 | 51 | 27 | 23 | 3 | 30 | 0 |
| BLACKBERRIES, RAW | 9042 | 69 | 24 | 0 | 5 | 0 | 0 | 0 | 0 | 4 | 0 |
| VITASOY COCOA | 137194 | 250 | 222 | 8 | 34 | 6 | 0 | 0 | 0 | 0 | 0 |
| ROASTED VEGETABLE PIZZA | 137260 | 698 | 1668 | 37 | 247 | 50 | 29 | 14 | 6 | 19 | 0 |
| POTATO LEEK SOUP | 137280 | 250 | 138 | 8 | 30 | 6 | 4 | 3 | 0 | 5 | 0 |
| SWEET CORN SOUP | 137281 | 228 | 228 | 9 | 32 | 7 | 3 | 2 | 1 | 2 | 0 |
| PLAN 4 | | 1495 | 2280 | 62 | 348 | 69 | 36 | 19 | 7 | 30 | 0 |
| AVOCADO, RAW, ALL VAR | 9037 | 45 | 68 | 1 | 1 | 7 | 4 | 1 | 1 | 3 | 0 |
| INSTANT SPICY BLACK BEAN SOUP | 109238 | 319 | 1135 | 56 | 155 | 8 | 3 | 1 | 1 | 52 | 0 |
| LIFEWAY KEFIR | 137196 | 250 | 185 | 24 | 24 | 6 | 0 | 0 | 0 | 0 | 2 |
| SPICY CHILI | 137263 | 900 | 753 | 32 | 76 | 23 | 14 | 7 | 2 | 28 | 0 |
| POTATO LEEK SOUP | 137280 | 250 | 138 | 8 | 30 | 6 | 4 | 3 | 0 | 5 | 0 |
| PLAN 5 | | 1764 | 2279 | 121 | 286 | 50 | 25 | 12 | 4 | 88 | 2 |

FIG. 6

SYSTEM AND METHOD FOR OPTIMIZED DIETARY MENU PLANNING

FIELD OF THE INVENTION

The present invention relates to the field of dietary menu planning, more particularly to a method and system for developing optimal dietary menus that maximize the palatability of the menu while satisfying dietary constraints.

BACKGROUND OF THE INVENTION

The particular problem of weight control is an acute one in Western society where a large proportion of society has been unable to balance their energy expenditure with their intake of calories. This is due in part to the generally sedentary lifestyle adopted in Western society and in part to the ready availability of foodstuffs, especially 'fast-foods' which are high in fats and sugars. Without adequate exercise, excess calories are converted and accumulated as body fat.

Excessive body weight and poor diet have been linked with obesity and a number of degenerative diseases, such as diabetes, coronary heart disease and some forms of cancer, and damage to macro- and micro-vascular systems and endothelial cells. An alarming proportion of society is, obese or suffers from long-term degenerative diseases. Moreover, obesity usually negatively impacts an individual's self esteem and can contribute to depression, anti-social behaviour and decreased productivity.

At any one time, a majority of North American adults are on a diet to attempt to lose weight. Unfortunately, many diets focus on immediate and rapid weight loss without providing an appropriate nutrient profile. Often these diets sacrifice palatability in favour of rapid calorie reduction, rendering them unsustainable over the long term. The result is usually an initial period of weight loss followed by a return to former eating habits because of the dieter's inability to maintain an unpalatable diet in the face of overwhelming food cravings. This creates the well known 'yo-yo' dieting effect which exacerbates the initial problem and has a negative impact on general physical health and individual self-esteem.

The problem is that individuals experience substantial difficulty in creating dietary menus that meet their specific dietary needs or goals. The most common dietary goal is body weight control, and in particular, weight loss, but an individual's dietary needs or goals can include glycemic control, blood lipid lowering or fecal bulking. The fact that people are having difficulty meeting this goal is evidenced by the proliferation of weight-loss advice, products and systems.

The difficulty people experience with creating dietary menus that meet their needs or goals is usually threefold. First, the person often lacks appropriate information about nutrition or an understanding of an appropriate nutrient profile. Second, the person is often uncertain as to what foodstuffs satisfy particular nutrient needs and in what quantity the foodstuffs should be eaten. Finally, typical dietary menus exclude the foods that people enjoy most and include the foods that people like to avoid, thereby rendering the menu unpalatable. As a result of this latter difficulty, a dietary menu plan is easily abandoned in favour of a person's old eating habits.

What is therefore required is a method of providing dieters with menus that meet the dietary constraints imposed by their particular health profile and by their particular physiological goals, but that also maximize the palatability of the resulting diet to the individual dieter. Such a system should be independent from the level of knowledge that a user has about the nutrient content of particular foodstuffs.

BRIEF SUMMARY OF THE INVENTION

The present invention provides a method and system that develops optimal dietary menus that maximize the palatability of the menu while satisfying dietary constraints. The dietary constraints are derived from an individual dieter's personal profile and physiological goals and from information regarding appropriate nutritional profiles.

In a first aspect, the present invention provides method of creating an optimized dietary menu for an individual, the method comprises the steps of: (a) receiving personal characteristics of the individual; (b) receiving a desired physiological change rate for the individual; (c) calculating dietary constraints, the dietary constraints being based upon the personal characteristics and the desired physiological change rate; (d) receiving food preferences for the individual; (e) creating the optimized dietary menu comprising a plurality of food items, and the food items being selected on the basis of the dietary constraints and the food preferences for the individual; and (f) outputting the optimized dietary menu.

In a second aspect, the present invention provides a system for creating optimized dietary menu planning for an individual, the dietary menu planning system comprises: (a) a user interface for receiving personal characteristics and food preferences for individual; (b) memory for storing the personal characteristics and the food preferences; (c) a food items database, the food items database including a plurality of food items; (d) a component operable to generate dietary constraints from the personal characteristics; (e) a component to create a dietary menu, the component being operable to select a plurality of food items for the dietary menu from the food items database wherein the selected food items maximize the food preferences of the individual and satisfy the dietary constraints; and (f a component operable to output the dietary menu to the individual.

In another aspect, the present invention provides a method for providing a dietary menu optimized for a client, the method comprises: storing personal information for the client, including information on personal characteristics for the client and information for a desired physiological rate of change for the client; storing food preferences for the client; calculating dietary constraints for the client, the dietary constraints being based upon the personal characteristics information and the dietary constraints information; providing a dietary menu to the client, the dietary menu being based on the calculated dietary constraints and the food preferences.

In a further aspect, the present invention provides a method for selling dietary menus, the method comprises the steps of: storing information for a plurality of clients, the information including identification information, personal characteristics and a desired physiological change rate; storing information on a variety of food items; receiving a request to purchase a dietary menu plan, the request including identification information for the client; receiving payment from the client; storing preferences of the client for the food items; calculating dietary constraints for the client based on the personal characteristics and the desired physiological change rate; generating a dietary menu comprising a number of the food items, the food items being selected on the basis of the dietary constraints and the preferences of the client.

In yet another aspect, the present invention provides a computer-readable signal embodied in a carrier wave, the carrier wave comprises: (a) a dietary menu plan code segment; and (b) the dietary menu plan code segment comprises a number of food items, the food items satisfying dietary constraints for an individual, and the food items maximizing food preferences of the individual.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Reference will now be made, by way of example, to the accompanying drawings which show preferred embodiments of the present invention, and in which:

FIG. 4 shows in table format a partial list of exemplary food items ranked by a user for the dietary menu planning system of FIG. 1;

FIG. 5 shows in table format a set of five menu plans generated by a system according to the present invention.

DETAILED DESCRIPTION OF THE PREFERRED EMBODIMENTS

Figure 1:
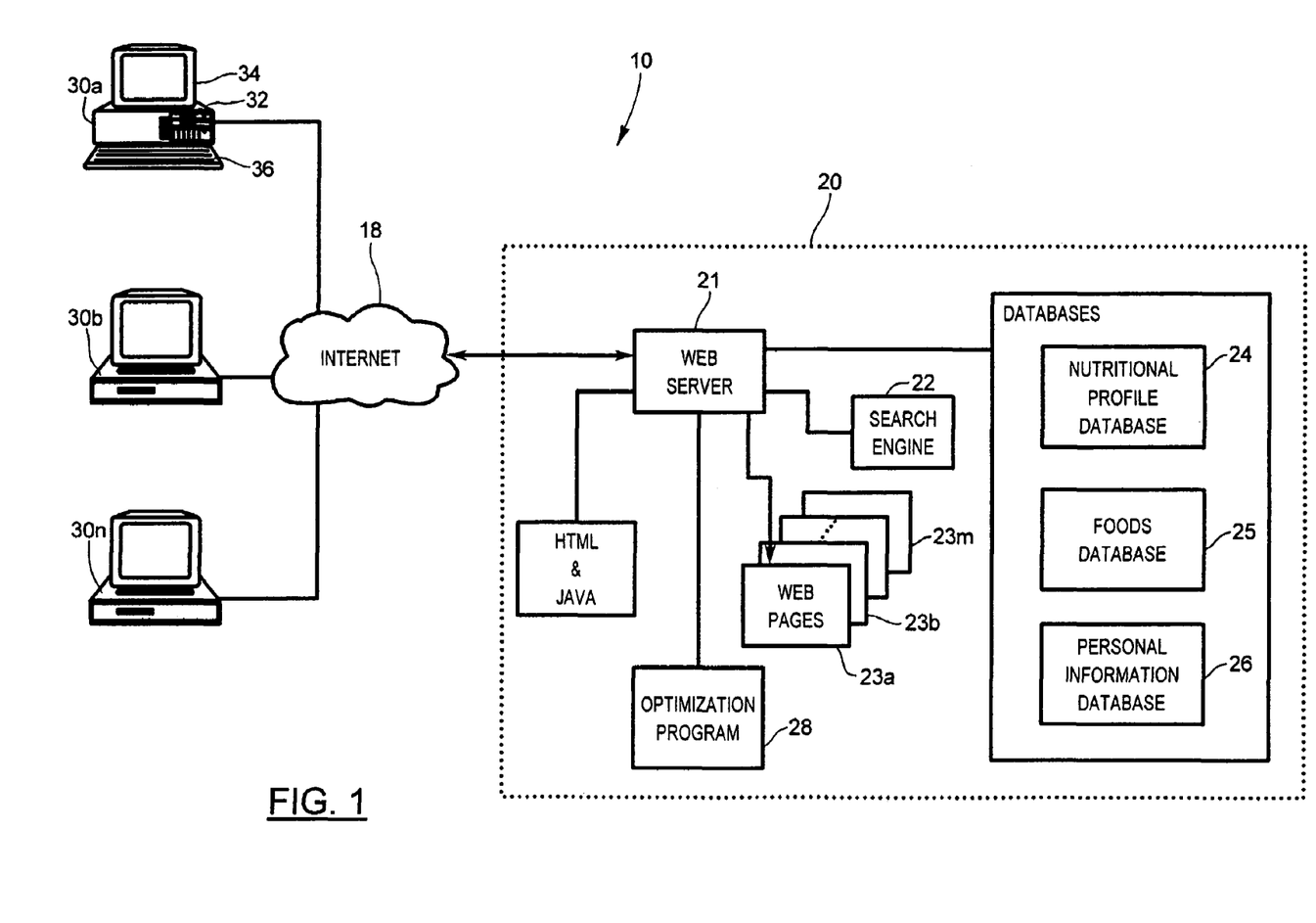
FIG. 1 shows in schematic form a system for a dietary menu planning and implementation for use in a networked environment according to the present invention.

Reference is first made to FIG. 1 which shows in schematic form a dietary menu planning system 10 according to the present invention.

According to one aspect of the invention, the dietary menu planning system 10 comprises an Internet or Web-based implementation. As shown in FIG. 1, the Web-based implementation of the dietary menu planning and implementation system 10 comprises a web site 20 and a number of user stations or computers 30, indicated individually by references 30a, 30b, . . . 30n. The web site 20 comprises a web server application or web server indicated by reference 21. The user stations 30 communicate with the web server 21 via the Internet 18.

The user stations 30 allow a client to access the service. As shown, the user station 30 includes a computer 32, a display unit 34 and an input device 36, such as a keyboard, mouse, microphone, touchpad or other suitable input device. For the Web-based implementation, the computer 32 runs a Web browser computer program for accessing the Web site 20 as will be described in more detail below. Alternatively, the network 18 could be a local-area network, a wide-area network or any other type of computer network, or combination of computer networks. The connection between the user stations 30 and the Internet 18 is typically made through a dial-up modem (not shown) attached to a communications port of the computer 32, conventional phone lines and an Internet service provider. Any other possible connection between the user stations 30 and the Internet 18 would be appropriate. While the system 10 is described in the context of a networked implementation, e.g. a client-server format, it will be appreciated that the system 10 may also be implemented as a stand-alone system.

As shown in FIG. 1, for a Web-based implementation, the server 21 includes web pages 23 which are downloaded through the Internet 18 and displayed on the user station 30 by the web browser program running on the computer 32. The web pages 23 provide an interactive interface which are designed to elicit required information from the user and to display enquiries and results. The web pages 23 may be implemented as Windows based screens with Hypertext markup language (HTML) fields or other suitable graphical user interface as will be familiar to one skilled in the art. As an alternative to web-based access, the user may retrieve a program resident on the server 21 through the Internet 18 for execution within the user station 30 alone, where the program operates to implement the dietary menu planning system 10. Other combinations are also possible, such as executing an application on the user station 30 in combination with program modules, databases or other programs resident on the server 21. Various combinations and configurations will be apparent to those skilled in the art.

Referring to FIG. 1, the server 21 at the web-site 20 includes a number of databases including a nutritional profile database 24, a foods database 25, and a personal information database 26. The server 21 also includes an optimization program 28. The server 21 may also include a search engine 22 for searching the various databases. The personal information database 26 stores personal information about each client or individual using the service. The information stored in the personal information database 26 includes an individual's sex, age, weight, height, and exercise level. As described in more detail below, the exercise level is based on a list of graded activities, i.e. by type and duration. The information in the personal database 26 is used to determine a metabolic rate for the individual and the daily energy required to keep the individual's body weight unchanged. The foods database 25 provides a collection of preferably over 10,000 food items which are widely available to a consumer and provide a wide variety of choice to suit the palate of many individuals who may subscribe to the service. The food items form the basis of dietary plan for the individual as will be described in more detail below. The nutritional profile database 24 stores nutritional parameters which are used by the optimization program 28 in formulating a dietary plan for the individual. The nutritional parameters may reflect recommended daily allowances of particular nutrients or food groups. The recommended daily allowances are typically guidelines developed by governments or non-governmental organizations.

The primary function of the optimization program 28 is to analyze the client or patient's personal information from the personal information database 26, including personal characteristics, desired rate of weight loss and food preferences. The optimization program 28 takes this information in conjunction with the nutritional parameters from the nutritional profile database 24 and foods from the food database 23 to create a dietary menu specific to the client. According to this aspect, the personal characteristics, the rate of weight loss and the nutritional parameters constitute a set of constraints, and the food preferences are expressed as an optimization function to be solved. The optimization program 28 solves the system of inequalities representing constraints while maximizing the optimization function such that the constraints are all satisfied and the palatability of the menu of food items is maximized for the user. The result is an optimal dietary menu for the user which, because of the inherent palatability (based on the user's preferences), has a high chance of being followed by the user over the longer term.

Figure 2:
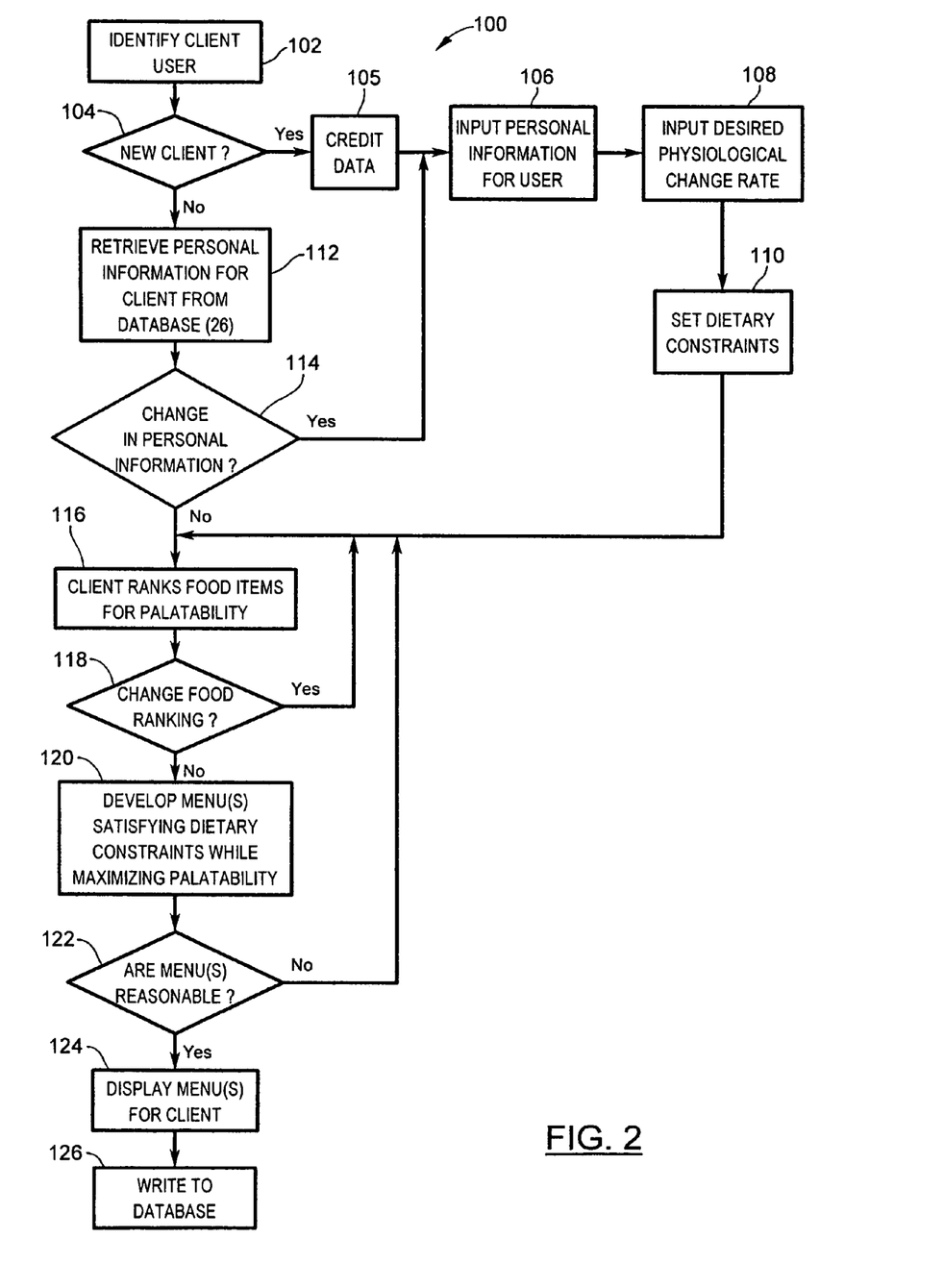
FIG. 2 shows in flow chart form a process or method for dietary menu planning according to the present invention.

Reference is next made to FIG. 2, which shows in flowchart form the steps comprising an optimized dietary menu planning process or method 100 according to the present invention. The first step in the optimized dietary menu planning process 100 as indicated by block 102 comprises a user, i.e. client or patient, accessing the system 10 (FIG. 1) through the user interface provided at one of the user stations 30 (FIG. 1). As described above, the user interface for the user station 30 may comprise a Web browser computer program, such as Internet Explorer™ or Netscape™ browsers, which runs on the computer 32. Through the web browser program, the user downloads web pages 23 from the web site 20. The first web page 23a preferably comprises a log-on screen or window in which the user identifies him/herself and logs onto the system 10. The user is prompted to either provide identifying information if he or she is a registered user or to register if he or she is a new user. To register and create an account, a user is prompted to provide identifying information such as their name, mailing address, e-mail address and phone number. A user may also be required to provide a password to secure access to individual personal profiles. If the user is a new client (decision block 104), then the user is prompted to input the required personal information, i.e. gender, height, weight, age and exercise level, as indicated by block 106. The procedure 100 may also include a credit payment step as indicated by block 105 to provide the capability for electronic commerce or e-commerce transactions to take place. For example, to bill users for use of the dietary menu planning system 10, a user may also be required to provide a valid credit card number or other credit or account information to enable payments to be made. It will be appreciated that various other security checks or credit checks may be incorporated into the initial account set-up and registration.

Next in step 108, the user inputs their desired physiological rate of change, for example, one pound per week. The user also indicates his or her energy expenditure by answering questions regarding his or her participation in various activities, the exertion level maintained and the duration of participation. The optimization process 100 utilizes this information to determine the user's metabolic rate and the daily energy required for the user to maintain his or her current weight. The rate at which the user wishes to lose (or gain) weight is used by the optimization process 100 to determine the daily energy required for the user to lose or gain weight at the desired rate. A simple approximation is that for each pound of weight loss desired per week, the user's daily energy requirement should be reduced by 500 Kilocalories.

Referring to FIG. 2, the optimization process 100 then determines dietary constraints (block 110) based on the information provided. The calculation of daily energy requirements as determined in block 108 provides a constraint on the daily number of calories that the user is permitted in his or her diet. This constraint is supplemented by other nutritional profile constraints such as the percentage of the calories that the user ought to obtain through protein, carbohydrates and fat. Further nutritional profile constraints can include the minimum amount of dietary fibre, the balance between monounsaturated versus saturated fats and the permitted amount of cholesterol intake. Various constraints and nutritional goals can be factored into the menu creation system as alternatives or as further linear constraints on the composition of the dietary menu. These constraints are derived from the parameters or nutritional guidelines contained in the nutritional profile database 24 (FIG. 1). The constraints imposed by a nutritional profile can be altered from time to time. The user could be given the opportunity to select from various nutritional or dietary profiles for use in the creation of his or her personal menus. In one embodiment, the nutritional profiles include profiles tailored to people with specific dietary needs, such as those suffering from type 2 diabetes, atherosclerosis, or various cancers. The dietary constraints are stored in the personal information database 26 (FIG. 1) as part of the personal information for the user or client.

By way of example, a user's personal information and desired rate of physiological change may dictate that the user consume no more than 2279 kilocalories per day. Other dietary constraints based upon the user's personal information and the nutritional profile may impose the requirements that protein constitute no more than 25% of the total daily energy intake, that carbohydrates constitute no more than 65% of the total daily energy intake and that fats constitute no more than 30% of the total daily energy intake. Additional constraints may include a minimum dietary fibre intake of 30 grams per day and a maximum dietary cholesterol intake of 190 units. With respect to fats, a constraint may be imposed that monounsaturated fats (MUFA) constitute at least 10% of the total daily energy intake while saturated (SFA) and polyunsaturated (PUFA) fats constitute no more than 16% of the total daily energy intake.

Nutritional constraints may be also tailored to accommodate special health considerations, such as diabetes. A user with diabetes would require a lower carbohydrate intake and a higher protein intake.

If the user is not a new client (decision block 104), i.e. the user is a registered user with a previously created a personal profile, then as indicated by block 112 the user logs onto the system 10 and the user's personal profile information is retrieved from the Personal Information database 26 (FIG. 1).

The user is then, in block 114 asked to verify the accuracy of the retrieved personal information. If the user's personal information has changed, then the user is routed to block 106 and is prompted to enter their up-to-date personal information and desired physiological change rate (block 108). The up-to-date personal information is then used to calculate the new dietary constraints (block 110).

According to one aspect of the invention, the various dietary constraints determined in block 110 present a system of inequalities that can be solved or satisfied by a number of menus. In order to maximize the palatability of the menus, the user is required to supplement their individual profile with information about their food likes and dislikes. As indicated in block 116, the next step involves the user ranking food items for palatability. Preferably, the user is presented with a multitude of individual food items and asked to score them numerically or categorize them qualitatively (for example, as described in FIG. 4 below). For example, a user might be presented with a food item and asked whether he or she "greatly likes", "likes", "tolerates", "dislikes" or "greatly dislikes" that particular item. In whichever fashion the ranking or scoring of food items is done, a food palatability profile is built up that is particular to that user. Obviously, the more food items presented to the user for ranking, the more accurate and detailed the palatability profile will be. The palatability profile contains information on the user's palatability scores of various food items.

Information on food items and their nutrient profiles is widely available. For instance, the USDA database contains information on well over 10,000 items. It will be appreciated that it would be too cumbersome to have the user rank all 10,000 items. Typically, the optimization process 100 is configured to present between 40 and 100 food items to the user for rating. An exemplary food item list is depicted in FIG. 4. The foods database 25 (FIG. 1) may be supplemented with additional items that are readily available to the users, such as pre-made dinners, so long as the necessary nutritional information is available for the item. In a situation where a set of users has the same basic set of food choices available to them, such as in a hospital or a clinic, the foods database 25 for those users could be adapted to contain only the items available in that specific situation.

Following ranking of the food items 116, the user is given an opportunity to change one or more food rankings 118. If the user is not satisfied with the food rankings developed in block 116, he or she may re-rank items previously ranked or rank additional items to create a more robust food palatability profile. The user may continue to rank or re-rank food items until the user is satisfied that an accurate food palatability profile has been developed.

Next in block 120, the optimization process 100 develops one or more menus which satisfy the dietary constraints (as determined in step 110) while at the same time taking into account or maximizing the rankings, i.e. palatability, of the food items (as determined in block 116). According to this aspect, the optimization process 100 comprises maximizing an optimization function that comprises the sum of the products of the palatability score accorded to individual food items and the physical weight of the serving of the individual food item. For instance, if a menu were designed to have four separate food items, then the optimization function would be the sum of four terms, each term being the product of a food item's palatability score and weight. The optimization process 100 seeks to identify four food items that maximize the value of the optimization function, i.e. maximize the amount of food palatable to the user, and yet satisfy all the linear constraints, such as the percentage of the menu composed of carbohydrates, fats or protein.

It will be appreciated that the optimization function may comprise alternative or additional parameters. In the preferred embodiment, the optimization function comprises the sum of terms, wherein each term is the product of an individual food items physical serving weight and palatability ranking. This form of the optimization function uses the weight of a food serving to maximize the quantity of highly palatable food in a generated menu plan. Alternatively, the optimization function may maximize the sum of terms wherein each term comprises the sum of an individual food item's palatability score and the food item's serving volume. Other variations will be apparent to those skilled in the art.

The optimization function may take the following form:

$$Z = p_1 w_1 + p_2 w_2 + p_3 w_3 + \ldots + p_n w_n \quad (1)$$

where $p_i$ is the palatability ranking of food item i, $w_i$ is the weight of food item i, and Z is the resultant palatability of the combination of food items 1 through n. The optimization process 100 seeks to maximize Z.

The system of dietary or nutritional constraints may take the following form:

$$a_{11}f_1 + a_{12}f_2 + a_{13}f_3 + \ldots + a_{1n}f_n < (>)(=)r_1 \quad (2)$$
$$a_{21}f_1 + a_{22}f_2 + a_{23}f_3 + \ldots + a_{2n}f_n < (>)(=)r_2$$
$$\ldots$$
$$a_{m1}f_1 + a_{m2}f_2 + a_{m3}f_3 + \ldots + a_{mn}f_n < (>)(=)r_m$$

where $r_j$ is restriction j, such as a maximum or minimum of some dietary variable, $a_{ji}$ is the contribution of food item i to restriction j, and $f_i$ is a quantity of food item i, such as its weight or its total energy.

For example, in the case of a dietary constraint x, which may specify that the total daily dietary fibre intake must be at least 30 grams, $r_x$ would be set to 30 grams and would be expressed as a minimum ($\geq r_x$) requirement. Additionally, each $f_i$ is the weight of food item i in grams, and each $a_{xi}$ is the percentage of food item i that constitutes dietary fibre. Accordingly, each term $a_{xi} f_i$ is the amount of dietary fibre in food item i expressed in grams.

Additional constraints can be used to deal with caloric inequalities and other nutritional factors to ensure a balance of items appears in the menu. For example, a constraint may impose the requirement that no more than two food items from a single category appear in a single menu. The food items may be classified, such as within the classes soup, fruit, dairy, snack, whole meal, or other classes. A constraint may be imposed that each menu have at least one item from the fruit class, the dairy class and the whole meal class. Additional classes or class-based constraints will be apparent to those skilled in the art. Other constraints that could be factored in are the guaranteed inclusion of certain food items and the guaranteed exclusion of others. In this manner, the dietary menu planning system 10 is able to accommodate allergies and other special needs.

To generate the menu(s), the optimization function is solved for a maximum, within the dietary constraints (block 110) and the palatability rankings (block 116). The resulting menu satisfies all the dietary requirements for the user to meet his or her weight loss goals and yet maximizes the potential that the user will find the food enjoyable.

The dietary menu planning system 10 can be used to create a single menu or multiple menus. Further constraints can ensure that food items are not repeated in a subsequent menu or are only repeated after a certain number of menus, so as to ensure variety in the diet. Ideally, the dietary menu planning system 10 can be used to create a set of menus for an entire week.

In one embodiment, in block 122 the dietary menu planning system 10 evaluates the reasonableness of the menu(s) created by the optimization process 100. The reasonableness of the menu may be determined with reference to any number of criteria, such as an assessment of the balance of classes of food items, or other indicia of a reasonable diet. Other assessments of reasonableness may occur at various points in the optimization process 100, including following the input of a desired physiological change rate 108 and following the ranking of food items for palatability. In the event that the dietary menu planning system 10 determines that the created menu(s) or the input provided by the client are unreasonable, then the system 10 returns the client to the ranking procedure 116 to either re-rank food items or to rank additional food items. Alternatively, if the source of the unreasonableness in the menu(s)

is the desired physiological change rate, the user may be returned to block 108 to input a more reasonable change rate.

The created menus may be displayed through the web browser operating on the user's computer 30 as indicated by block 124 (for example, in the form shown in FIG. 5, as detailed below). At this point, the user may print the menu using a printer (not shown) attached to the computer 30. The present invention may also write the user's menu(s) and personal information, including the palatability profile, to the database 26 (FIG. 1), as shown in block 126. This enables the user to re-access his or her menu(s) and his or her profile to create further menus without having to re-enter all of their personal data. This also allows for the possibility of tracking the user's progress over time and storing health information. A user could be prompted to enter his or her weight or other physiological data each time he or she accesses the system. The tracking of health information would assist in dietary research programs providing that the user consents to its use. The historical information can also provide the user with a record of his or her progress to assist him or her to evaluate the effectiveness of the dietary program and the reasonableness of his or her goals.

Another aspect of the invention, the dietary menu planning system 10 is suitable for producing weight-maintaining menus for existing users that have achieved their weight-loss goals and who wish to maintain a current weight. The objective of weight-maintaining menus is to prevent the 'yo-yo' effect of conventional weight-loss diets by enabling a user to design a palatable weight-maintaining menu.

The dietary menu planning system 10 as described above and depicted in FIG. 1 is suitable for use by multiple clients or users 30 through a computer network such as the Internet 18. Each client (i.e. user) has an individual profile which is saved in the personal information database 26 and the client may access the dietary menu planning system 10 through their computer 30 as required, independent of any of the other clients.

Figure 3:
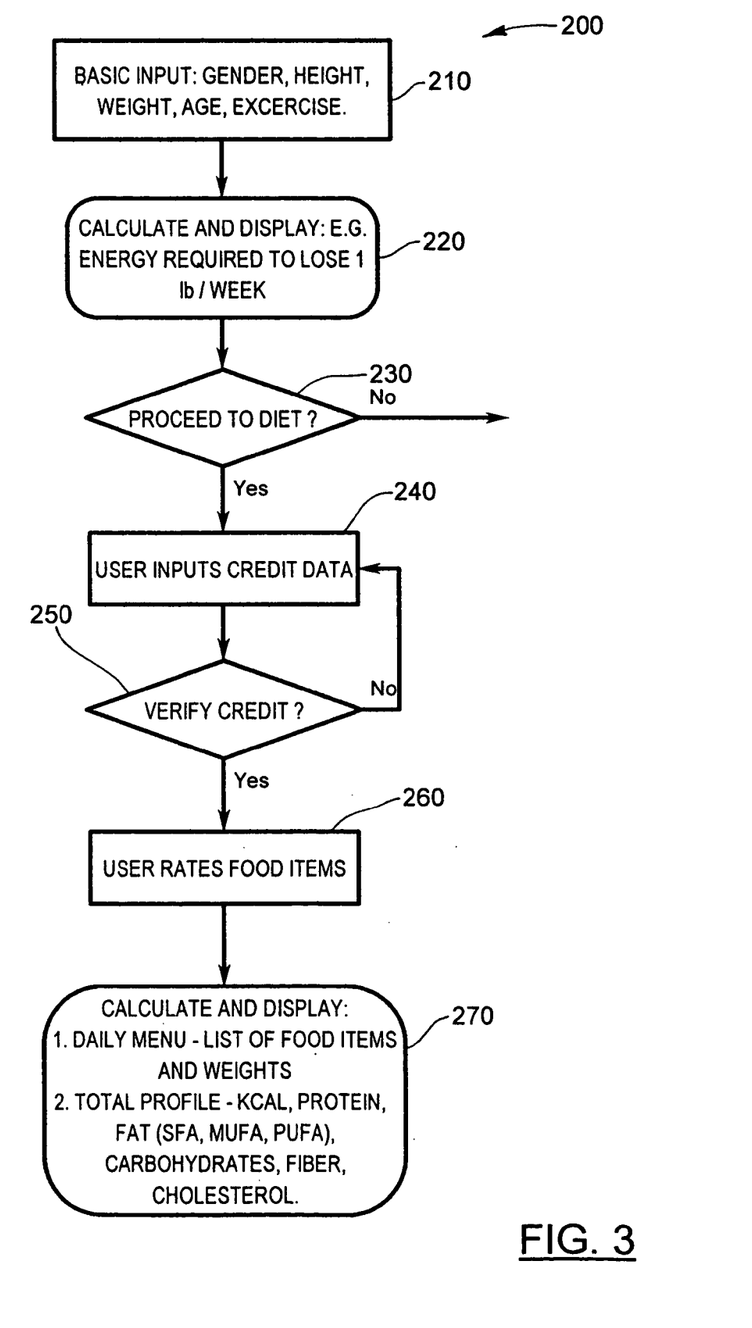
FIG. 3 shows in flow chart form a process for providing a dietary menu planning service according to another aspect of the present invention.

According to another aspect of the invention, access to the dietary menu planning system 10 is provided on a fee-for-service basis through the Internet. Under this arrangement, the user establishes an account and is billed for each menu created. Reference is made to FIG. 3 which shows in flow chart 200 form a fee-for-service implementation for the dietary menu planning system 10. The user accesses the Web server 21 (FIG. 1) over the Internet 18 (FIG. 1) through their computer 30. Once the user is connected to the Web server 21, i.e. on-line, the user is prompted to input basic information such as gender, height, weight, age and exercise (e.g. type(s), weekly frequency), as indicated in block 210. Based on the data inputted by the user, the system 10 calculates and displays the energy required to be expended by the user to, for example, lose 1 pound per week, as indicated in block 220. Next the user is prompted to proceed with a diet plan as indicated by decision block 230. It is at this step where the user decides whether to continue a pay a fee for the service of a diet plan. If the user is interested in proceeding further with a diet menu plan, then the user inputs their credit card data (or other form of electronic payment) in step 240. Security of the system is maintained through the use of data encryption and other security features well known to those skilled in the art. If the user is not interested in proceeding further, the user is free to leave, e.g. exit from the Web site or server 21 or log-off their computer 30. After the user inputs their credit or electronic payment data (block 240), an electronic payment transaction is initiated and if successful (block 250), the user proceeds to the rate, i.e. for palatability, food items presented by the dietary menu planning system 10, as indicated by block 260 in FIG. 3. The food items may be presented in a table of the form shown in FIG. 4.

As shown in FIG. 4, the food item table 300 comprises a food items column 310, a manufacturer column 320, and a rating column 330. The food items column 310 contains a list of food items which are retrieved from the foods database 25 (FIG. 1). The list of food items may be presented in terms of ethnic specific or vegetarian food items, for example. The manufacturer column 320 lists the manufacturer (i.e. brand name) or source of the food item. Preferably, food items which are widely available are selected for the foods database 25. This makes it easier for the user to try and buy the food items at their local grocery store. The rating column 330 shows the ratings for the food items selected by the user. The rating is an indication of the palatability of each one of the particular food item selected by the user. For example as shown in FIG. 4, "Bran Loaf" (reference 341, column 310) from Loblaws (column 320) has a relatively high rating of 36 (column 330), whereas "Barbecue Baked Potato Chips" indicated by reference 342 in column 310 have a relatively low rating of –55 (column 330).

Referring to FIG. 3, after the user has rated the food items presented in the food item table 300 (FIG. 4), the dietary menu planning system 10 generates and displays 270 one or more menu(s) tailored to the user dietary constraints and palatability preferences. The menu may be displayed graphically through the Web browser running on the user's computer 30, or alternatively, the menu may be sent to the user by email as enclosure in a printable file format such as Adobe™ PDF file. The menu includes a list of the food items selected by the user and the weights or amounts of the food items that the user may consume. The menu preferably also includes a total nutritional profile comprising kcal, protein, fat (SFA, MUFA, PUFA), carbohydrates, fiber and cholesterol, such as the exemplary menus shown in table form in FIG. 5.

As shown in FIG. 5, the menus table 400 lists five menus 402, 404, 406, 408 and 410. The menus table 400 includes a food item column 412, a food item code colunm 414, and a food serving weight column 416. It also includes food information in a kilocalories column 418, a protein column 420, a carbohydrates column 422, a fat column 424, a fibre column 432 and a cholesterol column 434. The information from the fat column 424 may be more specifically presented using a monounsaturated fats (MUFA) column 426, a polyunsaturated fats (PUFA) column 428 and a saturated fats (SFA) column 430. The values entered in each of the food information columns, except the kilocalories column 418, are expressed in grams.

Each menu 402, 404, 406, 408 and 410 lists the food items that make up the menu in the food items column 412. The listed food items are the foods that the user is permitted to eat in one day. The quantity of each food item, in grams, that the user is entitled to eat is listed in the food serving weight column 416. For example, menu one 402 lists five foods in rows 440, 442, 444, 446 and 448. The first row 440 of menu one 402 directs the user to eat 900 grams (column 416) of raw raspberries (column 412). In addition, menu one 402 directs the user to eat 199 grams (row 442, column 416) of taboule salad (row 442, column 412), 887 grams (row 444, column 416) of roasted vegetables in a pocket sandwich (row 444, column 412), 250 grams (row 446, column 416) of chocolate enriched rice beverage (row 446, column 412), and 250 grams (row 448, column 416) of black bean vegetable soup (row 448, column 412).

The exemplary menus table 400 is generated based upon a personal profile and physiological change rate that results in a target daily energy intake of 2279 kilocalories. Accordingly, the total kilocalories for each menu in the menu table 400 as shown in the kilocalories column 418 is no more than 2280 kilocalories.

Figure 6:
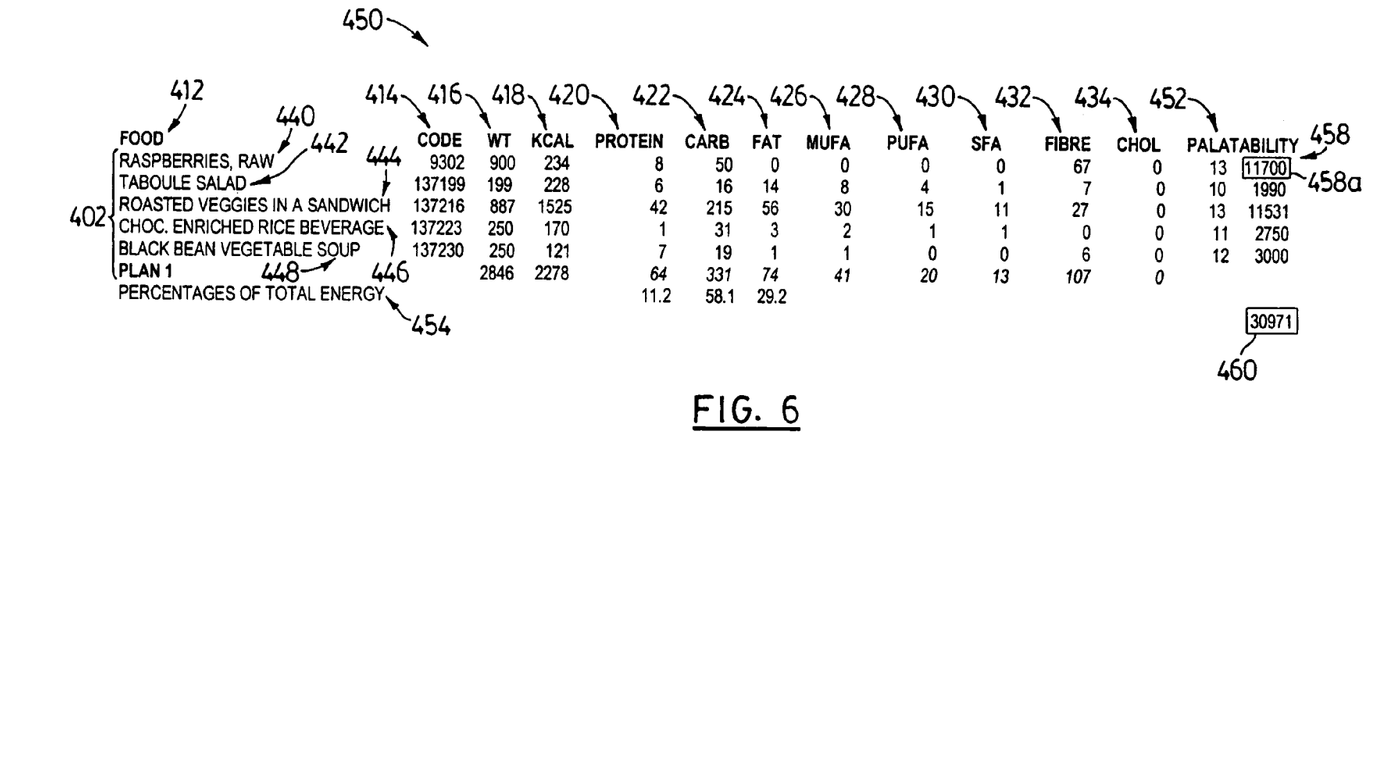
FIG. 6 shows in table format a menu plan generated by a system according to the present invention together with palatability information for the menu plan.

Reference is now made to FIG. 6, which shows a menu table 450 including menu one 402. The menu table 450 further includes a palatability column 452 containing the palatability ranking of each food item listed in the food item column 412. Also included in the menu table 450 is a product column 458 containing the product of the food item's weight (column 416) and the food item's palatability ranking (column 452). For example, in the case of 900 grams (column 416) of raw raspberries 440 having a palatability ranking of 13 (column 452), the product column entry 458a is 11700. The entries in the product column 458 are the terms of the optimization function that are added to produce the resultant palatability of the menu 460. The optimization process 100 (FIG. 2) seeks to maximize the resultant palatability of the menu 460.

Also shown in the menu table 450 are the percentages of total energy 454 contributed by particular components of the diet. For example, the percentage of total energy 454 contributed by protein (column 420) is 11.2%. The optimization process 100 (FIG. 2) may need to determine such percentages during menu development (block 120) to ensure compliance with some nutritional constraints. For example, a constraint used in the development of exemplary menu one 402 is that protein constitute no more than 25% of the total daily energy intake. Accordingly, the optimization process 100 (FIG. 2) must determine the energy attributable to protein in each food item, total those energies and determine what percentage of total energy constitutes protien.

Note that the example constraint given above is expressed as a percentage of total energy and not a percentage of total weight. The food information columns are expressed in grams of weight. Accordingly, each food information factor has an energy-weight conversion function. For example, each gram of protein contributes 4 kilocalories of energy. Accordingly, each term of the constraint is the product of the weight of protein (column 420) in the food item and the conversion function (multiplication by 4). The inequality is that the sum of the terms must be less than 25% of the total energy of the foods (column 418). The constraint may be expressed as:

$$\sum_{i=1}^{4} 4pw_i \le \frac{\sum_{i=1}^{4} kcal_i}{4} \quad (3)$$

where $pw_i$ is the weight of protein in each food item i (column 416) and $kcal_i$ is the kilocalories attributable to each food item i (column 418). Using the exemplary menu one 402, the constraint results in a sum of terms (4*8+4*6+4*42+4*1+4*7) equal to 256 and a requirement that the sum of terms be less than or equal to 2278/4, or 569.5. Accordingly, menu one 402 satisfies the constraint.

The access provided to the user in steps 210 and 212 (FIG. 3) serve to raise the interest level and market the diet menu planning system 10, but there may be instances where it is desirable to charge the user for any access to the system 10. Alternatively, access to the dietary menu planning system 10 could be licensed to institutional users, such as hospitals or clinics. Each institutional user may allow a number of its members or clients to use the system 10 and create personal profiles under the institutional license.

In yet a further embodiment, the dietary menu planning system 10 further incorporates a component for sending optimal menus approved by the user to a food provider, such as an on-line grocery delivery service at which the user maintains an account. The on-line grocery delivery service may then provide the user with a grocery delivery that includes all or a substantial portion of the food items listed in the approved menus. Additionally, the food items may be packaged by the food provider in the requisite quantities designated by the menus. This embodiment further ensures user compliance with the dietary menus by ensuring the designated food items are readily available.

Although the dietary menu planning system 10 is described in the context of a computer network 18 implementation as shown in FIG. 1, the dietary menu planning system 10 is also suitable for implementation in a stand-alone computer configuration. For the stand-alone configuration, the computer or user station 30 runs a computer program which provides the functionality of the dietary menu planning system 10 as described above with reference to the drawings. The stand-alone computer program is preferably implemented on a Windows™ based platform thereby providing a graphical user interface (GUI). The implementation details of the stand-alone embodiment will be within the understanding of those skilled in the art. The computer program may be provided to a user on computer readable media, such as a floppy disk or compact disk (CD). Alternatively, the computer program may be downloaded to the user's computer 30 through a network (for example the Internet 18—FIG. 1) from a server (for example, the web server 21 in FIG. 1) via a computer readable signal.

Advantageously, the dietary menu planning system 10 according to the present invention creates menus that maximize the palatability of the menu according to a particular user's individual tastes while satisfying all the user's dietary and nutritional constraints. The dietary menu planning system 10 allows a user to plan menus that achieve his or her physiological goals while at the same time providing menus which reduce the likelihood that the user will abandon the menus and fail to achieve his or her physiological goals for palatability reasons.

The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method of creating an optimized dietary menu for an individual using a computer having a processor, said method comprising the steps of:

receiving personal characteristics and a desired physiological change rate from the individual;

generating a set of dietary constraints based upon said personal characteristics using the processor, said desired physiological change rate, and nutritional profile constraints, wherein said set of dietary constraints comprises a system of inequalities;

receiving palatability scores for a plurality of food items, wherein each palatability score defines the palatability to the individual of the corresponding food item;

generating the optimized dietary menu comprising a set of food items selected from said plurality of food items using the processor, wherein said set of food items is selected so as to satisfy said system of inequalities and maximize a resultant palatability score associated with said set of food items; and outputting said optimized dietary menu, wherein said system of inequalities defines a relationship between said selected food items and one or more nutritional constraints, and wherein said step of generating the optimized dietary menu includes determining a quantity for each selected food item and maximizing an optimization function, wherein the optimization function comprises a sum of terms, and wherein each term comprises the product of the quantity and the palatability score associated with one of said selected food items, and wherein the result of said sum of terms comprises said resultant palatability score.

2. The method as claimed in claim 1, wherein, for each of said selected food items, said quantity comprises a serving weight for said selected food item.

3. The method as claimed in claim 1, wherein said system of inequalities includes two or more inequalities, and wherein each inequality comprises a sum of nutritional terms and a relation between the sum of nutritional terms and one of said nutritional constraints.

4. The method as claimed in claim 3, wherein said sum of nutritional terms comprises a sum of contributions of said selected food items to a nutritional variable for which said one of said nutritional constraints prescribes a maximum or minimum.

5. The method as claimed in claim 4, wherein said one of said nutritional constraints comprises a maximum total caloric intake.

6. The method as claimed in claim 4, wherein said one of said nutritional constraints comprises a minimum dietary fibre.

7. The method as claimed in claim 3, wherein said step of generating said set of dietary constraints includes obtaining one or more recommended daily maximums or minimums of particular nutrients from a nutritional profile database, and wherein said one or more recommended daily maximums or minimums comprise said nutritional constraints within said system of inequalities.

8. A system for creating an optimized dietary menu plan for an individual, said system comprising:

a food items database, said food items database including a plurality of food items;

a user interface for receiving a desired physiological change rate and personal characteristics of the individual and for receiving palatability scores for said plurality of food items for the individual, wherein each palatability score defines the palatability to the individual of the corresponding food item;

memory for storing said personal characteristics, said desired physiological change rate, and said palatability scores;

a component operable to generate a set of dietary constraints based upon said personal characteristics, said desired physiological change rate, and nutritional profile constraints, wherein said set of dietary constraints comprises a system of inequalities;

a component for generating the optimized dietary menu comprising a set of food items selected from said plurality of food items, said component being operable to select said set of food items so as to satisfy said set of system of inequalities and maximize a resultant palatability score associated with said set of food items; and a component operable to output said dietary menu to the individual, wherein said system of inequalities defines a relationship between said selected food items and one or more nutritional constraints, and wherein said component for generating the optimized dietary menu includes a component for determining a quantity for each selected food item and maximizing an optimization function, wherein the optimization function comprises a sum of terms, and wherein each term comprises the product of the quantity and the palatability score associated with one of said selected food items, and wherein the result of said sum of terms comprises said resultant palatability score.

9. The system as claimed in claim 8, wherein, for each of said selected food items, said quantity comprises a serving weight for said selected food item.

10. The system as claimed in claim 8, wherein said system of inequalities includes two or more inequalities, and wherein each inequality comprises a sum of nutritional terms and a relation between the sum of nutritional terms and one of said nutritional constraints.

11. The system as claimed in claim 10, wherein said sum of nutritional terms comprises a sum of contributions of said selected food items to a nutritional variable for which said one of said nutritional constraints prescribes a maximum or minimum.

12. The system as claimed in claim 11, wherein said one of said nutritional constraints comprises a maximum total caloric intake.

13. The system as claimed in claim 11, wherein said one of said nutritional constraints comprises a minimum dietary fibre.

14. A computer-readable medium having recorded thereon a computer readable program including instructions for creating an optimized dietary menu for an individual, said instructions comprising:

computer readable instructions for receiving personal characteristics and a desired physiological change rate from the individual;

computer readable instructions for generating a set of dietary constraints based upon said personal characteristics, said desired physiological change rate, and nutritional profile constraints, wherein said set of dietary constraints comprises a system of inequalities;

computer readable instructions for receiving palatability scores for a plurality of food items, wherein each palatability score defines the palatability to the individual of the corresponding food item;

computer readable instructions for generating the optimized dietary menu comprising a set of food items selected from said plurality of food items, wherein said set of food items is selected so as to satisfy said system of inequalities and maximize a resultant palatability score associated with said set of food items; and computer readable instructions for outputting said optimized dietary menu, wherein said system of inequalities defines a relationship between said selected food items and one or more nutritional constraints, and wherein said computer readable instructions for generating the optimized dietary menu include computer readable instructions for determining a quantity for each selected food item and maximizing an optimization function, wherein the optimization function comprises a sum of terms, and wherein each term comprises the product of the quantity and the palatability score associated with one of said selected food items, and wherein the result of said sum of terms comprises said resultant palatability score.

15. The computer readable medium as claimed in claim 14, wherein, for each of said selected food items, said quantity comprises a serving weight for said selected food item.

16. The computer readable medium as claimed in claim 14, wherein said system of inequalities includes two or more inequalities, and wherein each inequality comprises a sum of nutritional terms and a relation between the sum of nutritional terms and one of said nutritional constraints.

17. The computer readable medium as claimed in claim 16, wherein said sum of nutritional terms comprises a sum of contributions of said selected food items to a nutritional variable for which said one of said nutritional constraints prescribes a maximum or minimum.

18. The computer readable medium as claimed in claim 17, wherein said one of said nutritional constraints comprises a maximum total caloric intake.

19. The computer readable medium as claimed in claim 17, wherein said one of said nutritional constraints comprises a minimum dietary fibre.

20. The computer readable medium as claimed in claim 16, wherein said computer readable instructions for generating said set of dietary constraints include computer readable instructions for obtaining one or more recommended daily maximums or minimums of particular nutrients from a nutritional profile database, and wherein said one or more recommended daily maximums or minimums comprise said nutritional constraints within said system of inequalities.

* * * * *